United States Patent [19]

Branecky et al.

[11] 4,089,886

[45] May 16, 1978

[54] METHANOL PURIFICATION

[75] Inventors: Anthony J. Branecky, Kingsville; David W. Harris, Corpus Christi, both of Tex.

[73] Assignee: Celanese Corporation, New York, N.Y.

[21] Appl. No.: 817,751

[22] Filed: Jul. 21, 1977

[51] Int. Cl.² .............................................. C07C 29/24
[52] U.S. Cl. ..................................... 260/450; 423/417; 423/419 R; 568/915
[58] Field of Search ............................ 260/643 C, 450

[56] References Cited

U.S. PATENT DOCUMENTS

| | | | |
|---|---|---|---|
| 1,498,229 | 6/1924 | Buc | 260/643 C |
| 3,624,165 | 11/1971 | Dehn et al. | 260/450 |
| 3,780,163 | 12/1973 | Callighan et al. | 260/643 C |

FOREIGN PATENT DOCUMENTS

| | | | |
|---|---|---|---|
| 1,243,663 | 7/1967 | Germany | 260/643 C |
| 1,106,598 | 3/1968 | United Kingdom | 260/643 C |

OTHER PUBLICATIONS

Trout, "Journal of Chemical Education," (1939), pp. 453–459.
Dewar et al., "Royal Society Proceedings," Nov. 1905, pp. 558–577.

*Primary Examiner*—Joseph E. Evans
*Attorney, Agent, or Firm*—Stewart N. Rice; Ralph M. Pritchett

[57] ABSTRACT

Impure methanol may be treated to remove iron pentacarbonyl impurities by adding a source of hypochlorite ions to the impure methanol whereby the iron of the iron pentacarbonyl will be oxidized to the ferrous or ferric state. The impure methanol is then subjected to distillation to remove iron compounds as heavy ends.

10 Claims, No Drawings

4,089,886

METHANOL PURIFICATION

BACKGROUND OF THE INVENTION

The present invention relates to the purification of methanol containing iron pentacarbonyl impurities.

Methanol, particularly that produced by the reaction of carbon monoxide and hydrogen, generally contains small amount of iron pentacarbonyl as an impurity. The iron pentacarbonyl is apparently formed by reaction of iron present during the reaction, either in the catalyst or the reactor system itself, with carbon monoxide. The usual crude methanol, such as that produced by reaction of carbon monoxide and hydrogen, also generally contains various other impurities such as water, ethanol and the like which must be removed. Various systems have been devised to effect the removal of impurities from a crude methanol.

For example, U.S. Pat. No. 3,373,180 issued Mar. 12, 1968, to John Arnold Glass and Wilbert H. Urry and U.S. Pat. No. 3,433,841 issued Mar. 18, 1969, to John S. Dehn and John Arnold Glass disclose the removal of iron pentacarbonyl impurities by passing methanol through an ion exchange resin loaded with various metal ions. During the passage through the ion exchange resin, the iron of the iron pentacarbonyl (which is in a zero valent state) is oxidized to the ferrous state and retained on the resin bed. Such method is disadvantageous in that it involves the use of expensive ion exchange resins, and also in that it does not remove such impurities as waer and ethanol, thus necessitating another purification step to purify a crude methanol containing such other impurities.

The most widely used method of purifying a crude methanol is by distillation. In such a distillation, the volatile iron pentacarbonyl (which forms an azeotrope with methanol which is more volatile than methanol) is removed overhead and the methanol as bottoms. However, where distillation is utilized to purify a crude methanol containing iron pentacarbonyl impurities as well as high boiling impurities (that is higher boiling than methanol) such as water and ethanol, at least two distillation towers are required. That is, one distillation tower is required for removing the iron pentacarbonyl as light ends and another for removing the high boiling impurities. While the two-step distillation is effective, it would obviously be more desirable and more economical to effect the removal of the iron impurities as well as the high boiling impurities in a single distillation.

It is thus an object of the present invention to provide an improved method for removal of iron pentacarbonyl impurities from methanol. It is a further and particular object of the present invention to provide a method for purification of a crude methanol containing iron pentacarbonyl impurities as well as high boiling impurities involving only a single distillation step. It is a special object of the present invention to provide a method for purification of such a crude methanol which has been produced by the reaction of carbon monoxide and hydrogen. Additional objects will become apparent from the following description of the present invention.

SUMMARY

The present invention in one of its aspects is a process for purifying a crude methanol containing high boiling impurities which have a boiling point higher than that of methanol, such high boiling impurities including water, and also containing iron pentacarbonyl as an impurity, which process consists essentially of the successive steps of:

(a) combining said crude methanol in the liquid state with a source of hypochlorite ions will oxidize iron in said iron pentacarbonyl to a higher oxidation state; and, then (b) passing the crude methanol which has been so combined with said source of hypochlorite ions according to the preceding step (a) to a distillation column operated under such conditions that there is removed as vapors from an upper portion of said distillation column a methanol of improved purity, and, such that there is removed a liquid bottoms stream containing water, any other high boiling impurities, and iron compounds in said higher oxidation state, the iron of said iron compounds having been derived from said iron pentacarbonyl.

DETAILED DESCRIPTION OF THE INVENTION

According to the present invention, iron pentacarbonyl (which forms an azeotrope with methanol which is more volatile than methanol) in a crude methanol is converted to other iron compounds which are less volatile than methanol, thus allowing the iron impurities to be removed in the same distillation step as water and other high boiling impurities normally present in a crude methanol. As pointed out above, a crude methanol, particularly that produced by the reaction of carbon monoxide and hydrogen, will generally contain water and various other higher boiling impurities which must be removed in addition to the iron impurities present as iron pentacarbonyl. For example, a typical crude methanol may contain from about 5 to 25% by weight of water, from about 0.01 to 0.20% by weight of ethanol and from about 1 to 75 p.p.m. (parts per million) by weight of iron pentacarbonyl based on the weight of the impure methanol. Other impurities will usually also be present in very small amounts.

The conversion of the iron pentacarbonyl to less volatile iron compounds is accomplished by adding to the liquid, impure methanol a source of hypochlorite ions. The zero valent iron of the iron pentacarbonyl will react with the hypochlorite ions to convert the zero valent iron to a higher oxidation state. It is hypothesized that most of the zero valent iron is converted to the ferric state according to the following oxidation-reduction reaction:

$$3OCl^- + 3H_2O + 2Fe^\circ \rightarrow 3Cl^- + 2Fe^{3+} + 6OH^-$$

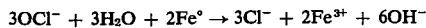

According to such reaction, 1.5 hypochlorite ions $(OCl^{31})$ is required for the oxidation of each iron atom of the iro pentacarbonyl. The inventors do not, however, wish to be limited by the foregoing hypothesis as they are not sure that all of the iron is oxidized to the ferric state, it being possible that some or all of the zero valent iron is converted to the ferrous state. In any event the zero valent iron is apparently oxidized to the ferrous or ferric state, and, in its higher oxodation state the iron will form iron compoundswhich are less volatile than the methanol. By the term "iron compounds" as used herein is meant to include complexes and the like. The iron compounds are probably iron chlorides or iron hydroxides, but such is not known wit certainty, and the inventors do not wish to be limited to such theory.

The source of the hypochlorite ions is not particularly critical although the source should not itself introduce additional impurities which will not be removed as heavy ends in the subsequent distillation step. The alkali metal hypochlorites or the alkaline earth metal hypochlorites are suitable sources of hypochlorite ions. As used in the specification and the claims the term "alkali metal" means sodium, potassium, lithium and rubidium, and, the term "alkaline earth metal" means calcium, barium, strontium and magnesium. Specific alkali and alkaline earth metal hypochlorites which may be utilized include solium hypochlorite, calcium hpochlorite, potassium hypochlorite, lithium hypochlorite and barium hypochlorite. Especially preferred of the alkali and alkaline earth metal hypochlorites is calcium hypochlorite.

Hypochlorite ions may also be formed in situ by addition of chlorine gas to the crude methanol, or an aqueous solution obtained by dissolving chlorine gas in water may be used as the source of hypochlorite ions. In practical application of the invention, the source of the hypochlorite ions should be added to the liquid, impure methanol in a fairly large excess, for example in an amount as to provide at least 50, and generally from about 75 to 200, hypochlorite ions per iron atom in the iron pentacarbonyl present.

The conditions under which the addition of the hypochlorite to the liquid, impure methanol is accomplished is not particularly critical and ambient conditions are satisfactory. In order to avoid the necessity of superatmospheric pressures to prevent boiling of the methanol, which has a normal boiling point of 64.65° C., the temperature of the impure methanol to which the hypochlorite source is added should generally be within the range of 5° to 60° C., preferably 10° to 35° C.

The effect of pH on the efficiency of the hypochlorite oxidation of the zero valent iron is negligable at the usual low levels of iron pentacarbonyl encountered in a crude methanol. However, since chloride ions ($Cl^-$) are produced in the oxidation-reduction reaction, it is preferred for corrosion control to adjust the pH to neutral or slightly above in order to prevent formation of hydrochloric acid. The pH adjustment of the crude methanol to neutral or slightly above (for example within the range of 7.0 to 8.0) should take place prior to the addition of the hypochlorite. A caustic solution may be used to adjust the pH.

The oxidation of the iron in the iron pentacarbonyl takes place fairly rapidly, and, the hypochlorite-treated crude methanol may be passed immediately to a distillation tower for separation of a methanol of improved purity as light ends or overheads. Such will be removed as vapors from an upper portion of the distillation tower, for example as overheads or as a side stream from an upper portion of the tower. Removed as heavy ends or bottoms from the distillation tower will be a liquid stream containing such high boiling impurities as water, ethanol and the like, as well as iron compounds derived from the iron pentacarbonyl. The iron in these iron compounds will be in the higher oxidation state.

The distillation may be conducted in conventional equipment utilizing standard and well known techniques. The distillation of a crude methanol to remove water, ethanol and the like are well known in the art and will not be repeated. The iron compounds in the higher oxidation state are less volatile than water and, therefore, no change needs to be made in a distillation column normally used for separating water from a crude methanol. Generally speaking, the distillation should be conducted at temperatures between 65° to 150° C. based on atmospheric pressure conditions. Of course, if other than atmospheric pressure is utilized, the boiling point of the components will be affected. Preferably the pressure in the distillation column will be between 1 and 2 atmospheres absolute.

The process of the present invention may be conducted batchwise or continuously, or a combination of the two. The following examples are given to illustrate the present invention, but are not to be construed as limiting the scope thereof. In the examples, all parts and percentages are by weight unless otherwise specified.

EXAMPLE 1

In accordance with prior art, a crude methanol was purified by distillation in a distillation tower containing 60 trays and operated at a bottom temperature of 102° C, an overhead temperature of 64° C, and an overhead pressure of one atmosphere absolute. The crude methanol contained about 15.2% by weight of water, 0.03 p.p.m. by weight of iron present as iron pentacarbonyl and 0.19 p.p.m. by weight of iron present in other forms. The crude methanol also contained very small amounts of other organic impurities such as methyl formate, methyl ether and ethanol. Before being introduced into the distillation tower, the pH of the crude methanol was adjusted to about 8.0 by the addition of an aqueous caustic solution. The crude methanol was passed to the 15th tray (measured from the bottom of the tower) at a temperature of about 30° C. Removed as liquid bottoms was a stream comprising mainly water, but also containing small amounts of other heavy ends and about 1.0 p.p.m. by weight of iron. Vapors were removed as a side stream from the upper portion of the distillation tower (from the 5th tray from the top of the tower) at a temperature of 64.5° C and condensed to provide a methanol of improved purity. The methanol thus recovered contained only about 0.03% by weight of water but undesirably contained about 0.02 p.p.m. by weight of iron.

EXAMPLE 2

The process of Example 1 was repeated with the exception that there was added to the crude methanol about 0.002 grams of calcium hypochlorite per kilogram of crude methanol so as to provide about 140 hypochlorite ions per iron atom present as iron pentacarbonyl. The calcium hypochlorite was added as a dilute solution in water. The purified methanol product contained about 0.10% by weight of water but less than 0.001 p.p.m. by weight of iron.

EXAMPLE 3

The process of Example 1 was repeated with the exception that, in accordance with the present invention, there was added to the crude methanol an aqueous solution obtained by dissolving chlorine gas in water. The aqueous solution thus obtained contained 0.010% by weight of chlorine and served as a source of hypochlorite ions. The amount of such aqueous solution added to the crude methanol was about 0.04 grams of aqueous solution per gram of crude methanol so as to provide about 100–200 hypochlorite ions per iron atom present in the crude methanol as iron pentacarbonyl. The purified methanol obtained by distillation contained about 0.10% by weight of water but less than 0.001 p.p.m. by weight of iron.

When chlorine gas is dissolved in water as in Example 3, the chlorine initially hydrolyzes very rapidly to form hydrochloric acid and hypochlorous acid. The hypochlorous acid then partially dissociates to hydrogen ions and hypochlorite ions. The three species $Cl_2$, HOCl, and $OCl^-$ exist together in equilibrium and each contributes to what is known as "free available chlorine" content. There relative proportions are determined by pH and temperature, and, the proportions are the same for any given set of conditions whether the chlorine is introduced as chlorine gas or a hypochlorite.

Theoretically, each mole of chlorine gas ($Cl_2$) dissolved in the water will provide one hypochlorite ion.

The embodiments of the invention in which an exclusive privilege is claimed are defined as follows:

1. A process for purifying a crude methanol containing high boiling impurities which have a boiling point higher than that of methanol, such high boiling impurities including water, and also containing iron pentacarbonyl as an impurity, which process consists essentially of the successive steps of:
    (a) combining said crude methanol in the liquid state with a source of hypochlorite ions under conditions whereby said hypochlorite ions will oxidize iron in said iron pentacarbonyl to a higher oxidation state; and, then,
    (b) passing the crude methanol which has been so combined with said source of hypochlorite ions according to the preceding step (a) to a distillation column operated under such conditions that there is removed as vapors from an upper portion of said column a methanol of improved purity, and such that there is removed a liquid bottoms stream consisting essentially of high boiling impurities including substantially all of the said water and also iron compounds in said higher oxidation state, the iron of said iron compounds having been derived from said iron pentacarbonyl.

2. The process of claim 1 wherein said source of hypochlorite ions is an alkali metal hypochlorite or an alkaline earth metal hypochlorite.

3. The process of claim 1 wherein said source of hypochlorite ions is chlorine gas or an aqueous solution obtained by dissolving chlorine gas in water.

4. The process of claim 1 wherein said source of hypochlorite ions is added in such amounts as to make available at least 50 hypochlorite ions per atom of iron in said iron pentacarbonyl impurities.

5. The process of claim 1 wherein said crude methanol has been produced by the reaction of carbon monoxide with hydrogen, and wherein said high boiling compounds include water and ethanol.

6. The process of claim 5 wherein said source of hypochlorite ions is added in such amounts as to make available from 75 to 300 hypochlorite ions per atom of iron in said iron pentacarbonyl impurities.

7. The process of claim 6 wherein said source of hypochlorite ions is an alkali metal hypochlorite or an alkaline earth metal hypochlorite.

8. The process of claim 7 wherein said source of hypochlorite ions is calcium hypochlorite.

9. The process of claim 6 wherein said source of hypochlorite ions is chlorine gas or an aqueous solution obtained by dissolving chlorine gas in water.

10. The process of claim 5 wherein the pH of said crude methanol is adjusted to a pH within the range of about 7.0 to 8.0 prior to the addition of the said source of hypochlorite ions.

* * * * *